United States Patent [19]
Werres

[11] Patent Number: 5,656,177
[45] Date of Patent: Aug. 12, 1997

[54] OIL-IN-WATER EMULSIONS AS SUBSTITUTES FOR MICROBICIDES (BIOCIDES) IN WATER CARRYING SYSTEMS

[75] Inventor: Joachim Werres, Drebber, Germany

[73] Assignee: Chemische Fabrik Stockhausen GmbH, Krefeld, Germany

[21] Appl. No.: 352,097

[22] Filed: Nov. 30, 1994

[30] Foreign Application Priority Data

Nov. 30, 1993 [DE] Germany .................. 43 40 665.3

[51] Int. Cl.$^6$ ........................................... C02F 1/50
[52] U.S. Cl. .................. 210/764; 210/749; 210/928; 162/161; 422/28
[58] Field of Search ................... 210/764, 928; 162/161; 422/28

[56] References Cited

U.S. PATENT DOCUMENTS

| | | | |
|---|---|---|---|
| 1,954,800 | 4/1934 | Cyr et al. | 210/764 |
| 3,006,807 | 10/1961 | Legator | 210/764 |
| 3,017,319 | 1/1962 | Rader | 210/764 |
| 3,052,594 | 9/1962 | Baker | 210/764 |
| 3,151,020 | 9/1964 | Cruickshank | 210/764 |
| 4,018,645 | 4/1977 | Takahashi et al. | 162/161 |
| 4,404,040 | 9/1983 | Wang | 422/28 |
| 4,715,980 | 12/1987 | Lopes et al. | 422/28 |
| 4,790,978 | 12/1988 | Allenmark et al. | 422/28 |
| 4,936,994 | 6/1990 | Wiatr | 210/764 |
| 4,954,338 | 9/1990 | Mattox | 424/405 |
| 5,441,723 | 8/1995 | Simmons | 422/28 |
| 5,444,078 | 8/1995 | Yu et al. | 422/28 |

FOREIGN PATENT DOCUMENTS

| | | | |
|---|---|---|---|
| 422948 | 4/1991 | European Pat. Off. | |
| 517360 | 5/1991 | European Pat. Off. | |
| 2530243 | 1/1977 | Germany | 422/28 |
| 132132 | 8/1978 | Germany | 422/28 |
| 97203 | 8/1981 | Japan | 210/764 |
| 1535841 | 1/1990 | U.S.S.R. | 210/764 |
| 2118925 | 11/1983 | United Kingdom | 210/764 |
| 2138798 | 10/1984 | United Kingdom | |

OTHER PUBLICATIONS

"Derwent Soviet Patents Abstracts", Week 9316, Section D–15, Abstract of SU 1730047–A1.
"Derwent Soviet Patents Abstracts", Week 9030, Section Q–4, Abstract of SU 1535841–A.

*Primary Examiner*—Neil McCarthy
*Attorney, Agent, or Firm*—Evenson, McKeown, Edwards & Lenahan P.L.L.C.

[57] ABSTRACT

The present invention relates to oil-in-water emulsions for the prevention of slime formation and for the reduction of microbial growth in water carrying systems. The emulsions comprise as component of the oil phase at least one of the following active substances:

a saturated or unsaturated, open-chain normal or isomeric hydrocarbon having 8–30 carbon atoms.

The emulsions have a proportion of the oil phase of 1 to 90 %-wt. and are used in an amount of 1 to 200 ppm and are free of toxic microbiocides.

9 Claims, No Drawings

OIL-IN-WATER EMULSIONS AS SUBSTITUTES FOR MICROBICIDES (BIOCIDES) IN WATER CARRYING SYSTEMS

The present invention relates to the use of agents for the prevention of slime formation caused by microorganisms and for the prevention of microbial growth in water-bearing systems.

Water carrying systems, such as water and waste water pipings, cooling or heating cycles, cooling lubricant systems, drilling fluids, or industrial process waters for the transport of matter contain a variety of microorganisms, such as bacteria of the genus *Pseudomonas vesicularis, Enterobacter cloacae, Citrobacter freundii* and *Enterobacter amnigenus* which grow rapidly owing to the conditions prevailing within these systems. As a result of the multiplication and metabolism of microorganisms, biological masses form in these media; for example, they adhere as bacterial mass or slimes to parts of plants, form sediments and are removed in the form of larger portions, and they result in disturbances in aggregates and production masses.

Particularly in papermaking, these processes during the production have to be prevented. At present, microbicides (biocides, slimicides) based on toxic substances having a strong action are being used for this purpose. According to J. Weigl, R. Grenz and H. L. Baumgarten "Grundlagen der Chemie für Papieringenieure", PTS-Verlag, München 1992, 5.2–5.45 and according to Papermaking Additives Committee of the Paper and Board Manufacture Division, Committee Assignment N° 5148, K. J. Hipolit, TAPPI PRESS 1992 (page 14), these substances are selected from specific bromine compounds, isothiazolones, dithiocarbonates, thiocyanates, and from specific organic sulfur compounds or cationics and inorganic compounds, such as sodium chlorite, sodium peroxide, sodium hydrogensulfite.

EP 562 739 A1 proposes to control slime formation by means of compositions containing glutaraldehyde and 2-(thiocyanomethylthio)-benzothiazole. EP 558 360 A1 proposes to use special disinfectants to fight bacteria strains of the genus Staphylococcus or Acinobacter.

DE 41 36 445 A1 describes the increase of the nitrogen and phosphate content in the aqueous medium in order to influence the growth of microorganisms under decomposition of already existing slimy substances and proposes to use sporadically known microbicides for this purpose, such as isothiazolones (tradename Kathoon), dibromonitrilopropionamide, or methylene bisisothiocyanate.

In addition to the problems with respect to the safe handling and the transport of these toxic substances and in view of the restriction of action to the desired range of application, it is necessary to use several of these microbicides in combination and in suscession in order to fight the resistance of the microorganisms to the product in use.

To recycle waste paper, EP 51 7 360 A1 describes the use of a mixture consisting of a surfactant and a hydrocarbon, in particular terpene, in order to inhibit tacky impurities in the pulp. Until today, volatile terpenoides are known to have an allelopathic action in plants.

Accordingly, it is the object of the present invention to provide substances or compositions for the prevention of slime formation and for the reduction of microbial growth in water carrying systems which, as compared to the known biocides and slimicides used for the same purpose, have a low toxicity, can easily be manufactured from readily available components and which are still reliably effective.

According to the present invention this object was achieved by using oil-in-water emulsions which are formed from a hydrophobic phase (oil phase), at least one emulsifier and water and which comprise in the hydrophobic phase at least one active ingredient which is selected from the following group of substances used alone or in admixture:

1. a saturated or unsaturated, open-chain or cyclic, normal or isomeric hydrocarbon having 8–30 carbon atoms,
2. a saturated or unsaturated fatty alcohol, a saturated or unsaturated fatty acid, a fatty acid monoalkyl ester, a fatty acid amide, or a fatty acid monoalkylamide of a saturated or unsaturated fatty acid, all of the compounds listed under 2. having 8 to 30 carbon atoms,
3. a mono- or polyester of a saturated or unsaturated fatty acid with 4 to 30 carbon atoms and monoalcohols and/or polyols, with the exception of polyethylene glycols,
4. a polyamide of saturated or unsaturated fatty acids having 8 to 30 carbon atoms and aliphatic polyamines having 2 to 6 nitrogen atoms,
5. an acyclic, preferably monocyclic and/or bicyclic terpene, in particular a terpene hydrocarbon and/or a terpene alcohol, and/or
6. a polyoxyalkylene compound based on alkylene oxides and $C_{12}$-$C_{18}$ fatty alcohols and/or $C_{12}$-$C_{18}$ fatty acids and/or fatty acid glycerides of $C_{12}$-$C_{18}$ fatty acids.

These oil-water emulsions are known from various fields. However, it was a surprise to find that these emulsions have the property of avoiding disturbances caused by bacterial masses or metabolic products, such as slimes in aqueous systems, in particular in papermaking.

Also, these oil-water emulsions are suitable for the use against microorganisms in aqueous systems in the manufacture of sugar from sugar beets.

The manufacture of the emulsions to be used according to the present invention, in particular of stable oil-in-water emulsions is known. To this effect, the oil component is emulsified in water by means of suitable known oil-in-water emulsifiers. The hydrophobic phase mainly represents the active substance.

Examples of hydrophobic oil components include:
— saturated hydrocarbons, such as octane, tetradecane, octadecane, eisodecane, decene, hexadecene, and technical alpha-olefins,
— fatty alcohols, such as octanol, dodecanol, tridecanol, hexadecanol, octadecanol, behenyl alcohol,
— fatty acids, such as capric acid, stearic acid, melissic acid, oleic acid, and linolenic acid,
— fatty acid esters, such as stearylic acid methyl ester, palmitic acid octadecyl ester, oleic acid octyl ester, glycerol mono- and trioleate, ethyleneglycol dilaurate, sorbitan stearates and oleates,
— fatty acid amides, such as stearylamide, coconut-fattyacid butyl-amide, acetic acid oleyl amide, and ethylene bisstearylamide.

Terpenes, such as menthol or orange-terpene (by Weißmer Baltische HG, Hamburg).

Additional suitable commercial hydrocarbons or hydrocarbon mixtures are liquid paraffin or mineral oil.

Additionally, fats and oils on a native basis, in particular vegetable oils and preferably rape-seed oil are suitable.

The saturated or unsaturated fatty alcohols which may be used as active ingredient according to the present invention are obtainable according to known methods, e.g., by oxo synthesis as oxoalchols or according to the Guerbet-reaction as Guerbet-alcohols.

The substances described, for example, in DE-AS 1 270 542 and EP 0 247 509 B1 are used as polyoxyalkylene compound based on alkylene oxides and/or fatty acid glycerides of $C_{12}$-$C_{18}$ fatty acids.

If terpenes are used, these are preferably used in admixture with a saturated or unsaturated fatty alcohol.

The proportion of the oil phase in the oil-water emulsion amounts to 1 to 90 %-wt., preferably 1 to 50 %-wt., and most preferably 5 to 30 %-wt. of the total emulsion. The emulsions to be used according to the present invention are non-toxic or only slightly toxic and may be classified in the Wassergefährdungsklasse 1 [water polluting class]. They are biodegradable and nonpolluting and, in particular when used in sewage treatment plants, they have no negative influence on the processes.

The agents to be used according to the present invention are employed as such or diluted with water or water and/or solvent-containing mixtures. The place of addition may be chosen at will, preferably the single or multiple or continuous addition to the water bearing system is effected at places where there is a high load by microbes or by their metabolic products, e.g., in papermaking, at the inflows of pulps consisting of waste paper portions or other recycling materials.

The added quantity of the oil-in-water emulsions amounts to 1–200 ppm, preferably 5–100 ppm, most preferably 10–50 ppm, relative to the total water carrying system.

The present invention will be illustrated by the following examples:

Manufacture of a Paraffin Emulsion A 14 kg paraffin (melting point: 48°–50° C.), 1.0 kg hexadecanol, 7 kg of a 75% paraffin sulfonate, and 2.1 kg water are homogeneously molten and then poured under stirring into a solution having a temperature of 60° C. and consisting of 74.5 kg water and 1.4 kg of an oleyl alcohol reacted with 20 moles of ethylene oxide. An oil-in-water emulsion results which has about 20.5% solid matter.

Manufacture of a Terpene Emulsion B

The same procedure as in the manufacture of emulsion A was used, with the difference that 14 kg terpene were used instead of paraffin.

EXAMPLE 1

In a papermaking machine, 400 g of the oil-in-water emulsion A, relative to 1 t of paper, was added to the 5% slush pulp flow, replacing the previously used bactericide Retardol 20, a commercial product of CHUPA GmbH, of D-86399 Bobingen, comprising as active ingredient alkyl benzyl ammonium chloride in aqueous solution.

After 15 days, the same quantity of Retardol 20 was used in turn; after 22 days, reconversion to the oil-water emulsion A was effected using the same quantity again.

The bacterial count in the diluted total stock was measured by using the bioluminiscence effect in luciferin/luciferase-ATP-oxidation according to the publication in "Wochenblatt für die Papierfabrikation" 23/24 (1980), pages 941–944, and expressed as "Relative Lichteinheit (RLU)" [relative light unit], with low RLU-values signifying a low bacterial number.

The data are listed in Table 1.

TABLE 1

| Day | RLU (thousand) | |
|---|---|---|
| 1 | 87 | Change to Emulsion A |
| 3 | 194 | |
| 5 | 174 | |
| 9 | 100 | |
| 14 | 85 | |
| 15 | 91 | Change to biocide |
| 17 | 215 | |
| 21 | 204 | |
| 22 | 280 | Change to Emulsion A |
| 24 | 245 | |
| 29 | 178 | |
| 31 | 80 | |
| 35 | 89 | |

The bacterial count increases for a short time, both when the change to the oil-in-water emulsion A and when the change to Retardol 20 is effected. Subsequently, the bacterial number is lowered by adding the oil-water emulsion A, with a level being achieved and maintained which corresponds to the conventional biocide. The bacterial growth is clearly inhibited. There was no slime formation during the test.

The manufacturing process took place without troubles and constantly resulted in the required paper quality.

Composition of the Emulsions C–M to be used according to the invention

| Composition | Oil Phase | | | Amount (%) | Water amount (%) |
|---|---|---|---|---|---|
| | | Amount (%) | | | |
| C | isohexadecane | 14.0 | fatty alcohol $C_{12}$-$C_{18}$ + 10 EO | 8.4 | 77.6 |
| D | oleic acid methyl ester | 14.0 | castor oil + 38 EO | 8.4 | 77.6 |
| E | oleic acid + 2 EO | 14.0 | castor oil + 38 EO | 8.4 | 77.7 |
| F | tall-oil fatty acid | 14.0 | castor oil + 38 EO | 8.4 | 77.6 |
| G | sorbitan monoisostearate | 14.0 | fatty alcohol $C_{12}$-$C_{18}$ + 10 EO | 8.4 | 77.6 |
| H | colza oil | 14.0 | castor oil + 38 EO | 8.4 | 77.6 |
| I | oleic acid triester of glycerol | 14.0 | castor oil + 38 EO | 8.4 | 77.6 |
| J | hexadecanol | 14.0 | castor oil + 38 EO | 8.4 | 77.6 |
| K | bisstearyl ethylene diamide | 14.0 | fatty alcohol $C_{12}$-$C_{18}$ + 10 EO | 8.4 | 77.6 |
| L | bone fat-PO[(1)] | 14.0 | fatty alcohol $C_{12}$-$C_{18}$ + 10 EO | 8.4 | 77.6 |
| M | dibutyl adipate | 14.0 | castor oil + 38 EO | 8.4 | 77.6 |

[(1)]corresponds to example 1 of EP 0247509 B1

EXAMPLE 2

The test according to Example 1 was repeated on a second papermaking machine using a modified composition. Instead of Retardol 20, 400 g of the oil-in-water emulsion A were added in the same quantity again. The bacterial count was conducted as in Example 1.

The data are listed in Table 2.

TABLE 2

| Day | RLU (thousand) | |
|---|---|---|
| 1 | 13.6 | Change to Emulsion A |
| 3 | 11 | |
| 5 | 30 | |
| 6 | 8 | |
| 7 | 6.6 | |
| 8 | 12 | |
| 10 | 11 | |

There was no slime formation. The production process proceeded without troubles.

EXAMPLE 3

On a papermaking machine of another manufacturer, instead of the biocides Daracide® and Daracide® (from Grace), 400 g of the oil-water emulsion B, relative to 1 t of paper, were added to a 5% sludge flow of waste paper in the same quantity. The exclusive use of waste paper normally results in a high germ load. The microbial count was effected in the backwater according to the counting method: German pharmacopeia, 10th edition, 1991, V.2.1.8, Examination as to microbial pollutants in non-sterile products.

The data are listed in Table 3.

TABLE 3

| Day | Total bacterial count/ml (in million) | |
|---|---|---|
| 1 | 42 | with 2 biocides |
| 2 | 54 | with 2 biocides |
| 3 | 38 | Change to emulsion B |
| 5 | 18 | |
| 7 | 1.6 | |
| 9 | 0.9 | |
| 11 | 1.5 | |
| 15 | 5.0 | |
| 18 | 6.1 | |
| 20 | 3.5 | |

By replacing the two previously used biocides for the oil-in-water emulsion B, the bacterial number could be lowered to 90% of the original value. No slime formation was observed and the production took place without troubles.

EXAMPLE 4

In a deinking plant hydrogen peroxide is used for bleaching purposes. The hydrogen peroxide used in the process is subject to premature decomposition owing to catalase-forming bacteria. For this reason the deinked paper has a poor brightness level if the hydrogen peroxide quantity is not increased to a considerable extent.

400 Emulsion A per ton of paper were dosed into the recycle water of the deinking plant, The development of bacteria in the recycle water was determined as in Example 1 by means of ATP-oxidation. The catalase amount was determined indirectly by means of removing the $H_2O_2$-quantity from the recyle water within 10 minutes, The results are listed in Table 4.

TABLE 4

| Day | RLU | $H_2O_2$-removal mg/l within 10 min. | |
|---|---|---|---|
| 1 | 3745 | 305 | start of dosage of Emulsion A |
| 2 | 1086 | 223 | |
| 3 | 286 | 27 | |
| 4 | 191 | 0 | |

The results show a considerable reduction in the bacterial count; the catalase-induced decomposition of the hydrogen peroxide is increasingly reduced or completely prevented.

EXAMPLE 5

In a waste paper recovery machine, wherein biocides are used only sporadically, 400 g of Emulsion C per ton of produced paper was added to the backwater. The bacterial count was effected as in Example 3. After one week, the bacterial count had declined from 7 million to 800,000 (−90%); there was no slime formation.

EXAMPLE 6

In a papermaking machine, which recovers paper pulp and waste paper and must be cleaned every week, 300 g of Emulsion E per ton of recovered paper was added to the backwater. The bacterial count was effected as in Example 3. After one week, the bacterial count had dropped by 65%. There was no slime formation, and the cleaning intervals could be extended to 14 days.

EXAMPLES 7 TO 9

Example 6 was repeated using Emulsions H, L, and M instead of Emulsion E:

| Emulsion | Quantity used | Decrease in bacterial count |
|---|---|---|
| H | 500 g | 50% |
| L | 450 g | 55% |
| M | 350 g | 90% |

There was no slime formation and the cleaning intervals could be extended.

EXAMPLE 10

15 ppm of Emulsion A was metered into the cycle water of a power station. The cycle water was severely polluted by bioslimes at the beginning of the experiment although biocides had been used. After 3 weeks, during which Emulsion A had been metered by 15 ppm and the biocide amount halved, the cycle water became significantly cleaner.

EXAMPLE 11

Instead of the previously intermittently dosage of 100 ppm of formalin, the composition B (Terpene Emulsion B) was used as microbicide substitute in the sugar industry. It was added to the extracted mash of chips by means of the countercurrent principle and into the extraction tower via dosage into the fresh water. The extraction of the sugar beet chips was effected at 70°–72° C. The added quantity of composition B continuously amounted to 25 ppm. The effect of the additive on the bacterial activity was determined analytically by determination of the lactate content produced by the bacteria in the raw juice behind the extraction mash, and in the raw juice from the middle of the extraction tower, as well as by measuring the pH-value of these juices.

The addition of 25 ppm of composition B clearly reduces the bacterial activity. In general, the added quantity will be selected such that a remaining lactate content ensures that the extracted beet chips may be pressed off to the desired degree of dryness. The experimental data are listing in the following Table 5:

TABLE 5

| Date | Time | Raw Juice Lactate mg/l | pH-value | Tower Lactate mg/l | pH-Value |
|---|---|---|---|---|---|
| 1st day | 9:00 a.m. | 674 | 5.7 | 731 | 4.8 |
| | 5:00 p.m. | 794 | 5.4 | 775 | 5 |
| | 11:00 p.m. | 752 | 5.8 | 789 | 5.8 |
| 2nd day | 1:00 a.m. | 733 | 4.8 | 778 | 4.9 |
| | 9:00 a.m. | 607 | 5.9 | 575 | 4.9 |
| | 5:00 p.m. | 401 | 6 | 359 | 5.3 |
| | 11:00 p.m. | 509 | 5.8 | 368 | 5.2 |
| 3rd day | 1:00 a.m. | 436 | 5.8 | 330 | 5.2 |
| | 9:00 a.m. | 589 | 5.5 | 371 | 5.1 |
| | 5:00 p.m. | 513 | 5.9 | 356 | 5.1 |
| | 11:00 p.m. | 627 | 5.7 | 379 | 5.1 |
| 4th day | 1:00 a.m. | 654 | 5.6 | 417 | 5 |
| | 9:00 a.m. | 790 | 5.5 | 656 | 4.9 |
| | 5.00 p.m. | 520 | 5.8 | 559 | 4.9 |
| | 7:00 p.m. | 581 | 5.7 | 520 | 5 |
| | 9:00 p.m. | 647 | 5.7 | 567 | 5 |
| | 11:00 p.m. | 723 | 5.5 | 615 | 4.9 |
| 5th day | 1:00 a.m. | 743 | 5.6 | 587 | 4.8 |
| | 9:00 a.m. | 411 | 5.8 | 400 | 5.1 |
| | 5:00 p.m. | 626 | 5.6 | 488 | 5 |
| | 11:00 p.m. | 617 | 5.7 | 515 | 5 |
| 6th day | 1:00 a.m. | 689 | 5.6 | 620 | 4.9 |
| | 9:00 a.m. | 409 | 5.9 | 498 | 5.2 |
| Average Values | | 610.65 | 5.67 | 537.13 | 5.05 |

The experimental data prove that the results clearly remain below the previously accepted upper limit of lactate of 800 mg/l in the formalin dosage and that low sugar losses can be achieved even without the addition of formalin.

I claim:

1. A method of decreasing microbial growth and preventing slime formation in an aqueous medium comprising the step of incorporating in said aqueous medium an effective microbial growth retarding and slime formation preventing amount of an oil-in-water emulsion comprising an oil phase and at least one emulsifier for the oil phase, wherein the oil phase comprises saturated or unsaturated, open-chain, normal or isomeric hydrocarbons containing 8 to 30 carbon atom; and wherein said emulsion is free of toxic microbiocides.

2. The use of the oil-in-water emulsion according to claim 1 in papermaking.

3. A method according to claim 1, wherein the oil phase comprises at least one saturated hydrocarbon selected from the group consisting of octane, tetradecane and octadecane, or at least one unsaturated hydrocarbon selected from the group consisting of decene or hexadecene, or at least one technical alpha-olefin.

4. A method according to claim 1, wherein the oil phase comprises from 1 to 90 %-wt. of the emulsion.

5. A method according to claim 4, wherein the oil phase comprises from 1 to 50 %-wt. of the emulsion.

6. A method according to claim 5, wherein the oil phase comprises from 5 to 30 %-wt. of the emulsion.

7. A method according to claim 1, wherein from 1 to 200 ppm of the oil-in-water emulsion is incorporated into the aqueous medium.

8. A method according to claim 7, wherein from 5 to 100 ppm of the oil-in-water emulsion is incorporated into the aqueous medium.

9. A method according to claim 8, wherein from 10 to 50 ppm of the oil-in-water emulsion is incorporated into the aqueous medium.

* * * * *